United States Patent
Wood et al.

(10) Patent No.: US 11,179,314 B2
(45) Date of Patent: Nov. 23, 2021

(54) LIQUID COMPOSITION COMPRISING HAIR DIRECT DYES

(71) Applicant: KAO GERMANY GMBH, Darmstadt (DE)

(72) Inventors: Jonathan Wood, Darmstadt (DE); Anja Aechtner, Darmstadt (DE); Sandra Schmelz, Darmstadt (DE); Frank Kufner, Darmstadt (DE)

(73) Assignee: KAO GERMANY GMBH, Darmstadt (DE)

( * ) Notice: Subject to any disclaimer, the term of this patent is extended or adjusted under 35 U.S.C. 154(b) by 350 days.

(21) Appl. No.: 16/487,874

(22) PCT Filed: Nov. 9, 2017

(86) PCT No.: PCT/EP2017/078705
§ 371 (c)(1),
(2) Date: Aug. 22, 2019

(87) PCT Pub. No.: WO2018/087203
PCT Pub. Date: May 17, 2018

(65) Prior Publication Data
US 2021/0275432 A1 Sep. 9, 2021

(30) Foreign Application Priority Data
Nov. 11, 2016 (EP) .................... 16198348

(51) Int. Cl.
| *A61Q 5/10* | (2006.01) |
| *A61K 8/898* | (2006.01) |
| *A61K 8/34* | (2006.01) |
| *A61K 8/23* | (2006.01) |
| *A61K 8/22* | (2006.01) |
| *A61K 8/41* | (2006.01) |

(52) U.S. Cl.
CPC ............... *A61K 8/898* (2013.01); *A61K 8/22* (2013.01); *A61K 8/23* (2013.01); *A61K 8/345* (2013.01); *A61K 8/41* (2013.01); *A61Q 5/10* (2013.01); *A61K 2800/4324* (2013.01); *A61K 2800/882* (2013.01)

(58) Field of Classification Search
CPC .... A61Q 5/10; A61K 8/22; A61K 2800/4324; A61K 2800/882; A61K 8/345; A61K 2800/43; A61K 2800/31; A61K 2800/432; A61K 8/89; A61K 8/898; A61K 8/41
USPC ............................................................ 8/405
See application file for complete search history.

(56) References Cited

U.S. PATENT DOCUMENTS

| 2010/0037404 A1* | 2/2010 | Koike ................. A61K 8/891 8/423 |
| 2010/0037909 A1* | 2/2010 | Gross .................. A61Q 5/10 132/208 |
| 2010/0212092 A1* | 8/2010 | Agarelli ............... A61K 8/42 8/405 |
| 2010/0275387 A1* | 11/2010 | Charrier .............. A61Q 5/08 8/407 |
| 2012/0180230 A1* | 7/2012 | Schmenger ......... A61Q 5/08 8/405 |
| 2014/0298595 A1* | 10/2014 | Weser ................. A61Q 5/065 8/405 |
| 2017/0196792 A1 | 7/2017 | Nojiri |

FOREIGN PATENT DOCUMENTS

| DE | 33 15 522 A1 | 11/1983 |
| EP | 0 868 902 A2 | 10/1998 |
| EP | 2 606 873 A1 | 6/2013 |
| WO | 95/15144 A1 | 6/1995 |
| WO | 2008/106417 A1 | 9/2008 |
| WO | 2015/186816 A1 | 12/2015 |

OTHER PUBLICATIONS

English transaltion of the Patent No. EP0868902 A2 (Jun. 22, 2021).*
International Search Report dated Nov. 9, 201, in connection with PCT International Application No. PCT/EP2017/078705.

* cited by examiner

*Primary Examiner* — Eisa B Elhilo
(74) *Attorney, Agent, or Firm* — Norris McLaughlin, P.A.

(57) ABSTRACT

The present invention relates to a stable liquid composition comprising hair direct dyes in a liquid diol which is used for dyeing hair after mixing with one or more other aqueous compositions. The compositions preferably comprise an alkalizing agent.

14 Claims, No Drawings

LIQUID COMPOSITION COMPRISING HAIR DIRECT DYES

This application is the U.S. National Stage of International Application No. PCT/EP2017/078705, filed Nov. 9, 2017, which claims foreign priority benefit under 35 U.S.C. § 119 of European Application No. 16198348.1 filed Nov. 11, 2016 the disclosures of which are incorporated herein by reference.

The present invention relates to a stable liquid composition comprising hair direct dyes which is used for dyeing hair after mixing with one or more other aqueous compositions.

Dyeing hair using direct dyes have been known for many years. Direct dyes are usually comprised in an aqueous medium which are applied onto hair and after leaving certain period of time on the hair, rinsed off from hair. There are also dyeing compositions available which may be left on the hair. It has further been observed that some of the direct dyes, if not all, may not be stably stored in such aqueous medium as they crystalize out during storage and, therewith, the dyeing performance of the composition is reduced and/or the shade intended to be achieved may not be the result of the dyeing process.

Known solution to the above problem has been addition of the direct dyes in powder form prior to use into the aqueous compositions. This is not at all efficient as, at the time of use, the dissolving process may not be controlled and some of the dyes are simply left as undissolved in the aqueous medium and, therefore, dyeing results are unsatisfactory. On the other hand, in order to dissolve solid dyes, large amount of aqueous medium may be required so that the target dye concentration may not be reached.

In order to solve the storage stability of the direct dyes in a liquid medium which may as well be mixed into any aqueous and/or anhydrous compositions easily and effectively, the inventors of the present invention have unexpectedly found out that the direct dyes dissolved in a liquid diol may stably be stored for a long period of time. The liquid composition must be substantially anhydrous and therefore must not comprise high level of water.

Thus, the first object of the present invention is a composition for keratin fibres, preferably human keratin fibres, especially human hair, which is liquid at 20° C., comprising one or more direct dyes, one or more diols, which is (are) liquid at 20° C., at a total concentration more than or equal to 50% by weight, and 2% by weight or less, preferably 1% by weight or less water wherein all concentrations are calculated to the total composition.

The compositions of the present invention comprises one or more direct dyes which may be selected from cationic, anionic and non-ionic dyes.

Suitable anionic direct dyes are Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium, potassium. Among those, the most preferred anionic dyestuffs are Acid Red 52, DC Violet 2, DC Red 33, DC Orange 4, DC Red 27, DC Yellow 10, HC Blue 18, HC Red 18, and HC Yellow 16.

Suitable cationic dyes are in principle those available on the market for cosmetic hair colouring applications. For this purpose, special reference is made to the PCT application WO 95/15144 of Ciba-Geigy AG. Some examples to those are Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green 1, Basic Red 2, Basic Red 12 Basic Red 22, Basic Red 76, Basic Violet 1, Basic Violet 2, Basic Violet 3, Basic Violet 10, Basic Violet 14, Basic Yellow 57, Basic Red 51, Basic Yellow 87, HC Blue 17 and Basic Orange 31. The most preferred ones are Basic Red 51, Basic Yellow 87 Basic Orange 31, HC Blue 17 and Basic Blue 124.

Suitable neutral dyes including nitro dyes are HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid.

The most preferred dyes of the present invention are HC Blue 18, HC Red 18, and HC Yellow 16.

The composition comprises one or more hair direct dye at a total concentration of 0.001% to 10% by weight, preferably 0.005% to 9% by weight, and more preferably 0.01% to 7.5% by weight, calculated to the total of the composition. The composition can also comprise a mixture of several direct dyes, i.e., an anionic, a cationic and/or nonionic ones. In such a case the dyes may be mixed at any ratio with each other.

The direct dyes may be present as dissolved or partially dissolved in one or more liquid diols. The preferred is that the direct dyes are present as dissolved.

The composition of the present invention comprises one or more diols selected from $C_2$-$C_6$ diols, and linear or branched polymerization products of ethylene oxide and/or propylene oxide with a terminal OH group at both ends, and mixtures thereof.

Suitable $C_2$-$C_6$ diols are ethylene glycol, propylene glycol, butylene glycol, pentylene glycol and hexylene glycol.

Suitable linear or branched polymerization products of ethylene oxide with a terminal OH group at both ends are PEG-4, PEG-6, PEG-7, PEG-8, PEG-9, PEG-10 and PEG-12.

Suitable linear or branched polymerization products of propylene oxide with a terminal OH group at both ends are PPG-3, PPG-6, PPG-7 and PPG-9.

The most preferred diol is propylene glycol also known as 1,2-propylene glycol and 1,2-propylene glycol. Especially preferred is 1,2-propylene glycol.

The composition comprises one or more diols liquid at 20° C. at a total concentration more than or equal to 50% by weight, preferably in the range of 55 to 90% by weight, more preferably 60 to 90% by weight, calculated to the total composition.

The composition of the present invention preferably comprises an alkalizing agent. The suitable ones are alkanolamines according to the general structure $R_4 \ R_5 \ R_6 \ N$ wherein $R_4$, $R_5$ and $R_6$ are same or different H, $C_1$ to $C_4$ alkyl, $C_3$ to $C_4$ unsaturated alkyl, $C_3$ to $C_4$ branched alkyl, $C_1$ to $C_4$ hydroxy alkyl, $C_3$ to $C_4$ unsaturated hydroxy alkyl, $C_3$ to $C_4$ branched hydroxy alkyl, preferably with the condition that at least one of $R_4$, $R_5$ or $R_6$ is different from H.

Suitable alkalizing agents are ammonia, monoethanolamine, diethanolamine, triethanolamine, monoethanol methylamine, monoethanoldimethylamine, diethanolmethylamine, monoethanolethylamine, monoethanoldiethylamine, diethanolethylamine, monoethanolpropylamine, monoethanoldipropylamine, diethanolpropylamine, monoethanolbutylamine, aminomethyl propanol and diethanolbutylamine. Preferred alkalizing agents are monoethanolamine and/or aminomethyl propanol. The most preferred is aminomethyl propanol abbreviated as AMP.

The alkalizing agent is comprised in the compositions at a total concentration of 0.5 to 15%, preferably 1 to 10%, more preferably 1.5 to 7.5% and most preferably 2 to 7.5% by weight calculated to the total of the composition.

The composition may comprise one or more aminosilicone, preferably selected from the following compounds a. a compound according to the general structure

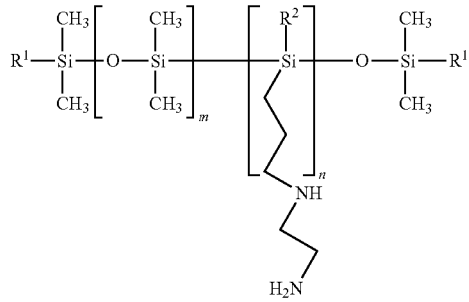

wherein R1 is selected from OH, OCH3, and/or O—Si—$(CH_3)_3$, R2 is selected from $CH_3$, $OCH_3$, O—$(Si$—$(CH_3)_2)$ x-$R^1$, and/or O—Si—$(CH_3)_3$, with the provision that if $R^1$ or $R^2$ are selected from O—Si—$(CH_3)_3$, then all other $R^1$ or $R^2$ are selected from O—Si—$(CH_3)_3$ and/or $OCH_3$.

b. silicone graft copolymer comprising an organopolysiloxane segment as a main chain thereof and an unsaturated monomer-derived polymer segment as a side chain thereof, which is obtainable by firstly reacting an aminopropyl dimethicone with the thiolactone of acetyl homocysteine and then graft copolymerizing the thus obtained mercapto modified dimethicone with a mixture of N,Ndimethylacrylamide and N-t-butylacrylamide, c. an organopolysiloxane, wherein at least two silicon atoms in an organopolysiloxane segments constituting a main chain of the organopolysiloxane are bound to poly(N-acyl-alkyleneimine) segments consisting of repeating units represented by the following general formula via alkylene group containing hetero atom:

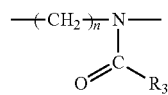

wherein $R_3$ is a hydrogen atom, an alkyl group having 1 to 22 carbon atoms, an aralkyl group, or an aryl group; and n is 2 or 3; wherein the number-average molecular weight of the poly-(N-acylalkyleneimine) segment is from 1,200 to 5,500, wherein the weight ratio of the organopolysiloxane segments (a) constituting the main chain to the poly-(N-acylalkyleneimine) segments (b) i.e., a/b is from 35/65 to 60/40, wherein the weight-average molecular weight of the adjacent poly-(N-acylalkyleneimine) segments is from 1,300 to 5,500, and wherein the weight-average molecular weight of the organopolysiloxane segment constituting the main chain is from 7,000 to 100,000.

Suitable examples are amodimethicone as known and delivered by various suppliers and polysilicone-9 supplied by Kao Corporation.

The total concentration of one or more amino silicones in the compositions is in the range of 0.01 to 2.5% by weight calculated to the total of the composition.

The pH of the compositions is in the range of 8 to 12, preferably in the range of 9 to 11 measured as a 10% by weight solution in demineralized water at 20° C.

Compositions according to the present invention can further comprise surfactants selected from anionic, nonionic, amphoteric and/or cationic surfactants. The anionic, nonionic, amphoteric surfactants are used generally as emulsifier or solubilizer. The presence of surfactants may further contribute to miscibility of the compositions into another composition which may be anhydrous and/or aqueous. On the other hand, the cationic surfactants do provide the same benefits as the other surfactants but are at the same time particularly used as hair conditioners.

Anionic surfactants suitable are in principle known from the cleansing compositions. These are anionic surfactants of the sulfate, sulfonate, carboxylate and alkyl phosphate type, for example, the known $C_{10}$-$C_{18}$-alkyl sulfates, and in particular the respective ether sulfates, for example, $C_{12}$-$C_{14}$-alkyl ether sulfate, lauryl ether sulfate, especially with 1 to 4 ethylene oxide groups in the molecule, monoglyceride (ether) sulfates, fatty acid amide sulfates obtained by ethoxylation and subsequent sulfatation of fatty acid alkanolamides, and the alkali salts thereof, as well as the salts of long-chain mono- and dialkyl phosphates. Preferred anionic surfactants are alkyl sulphate surfactants especially lauryl sulphate and its salts.

Further suitable surfactants are nonionic surfactants. Non-limiting examples are long-chain fatty acid mono- and dialkanolamides, such as coco fatty acid mono- or diethanolamide and myristic fatty acid mono or diethanolamide, stearic acid mono or diethanolamide, alkyl polyglucosides with an alkyl group of 8 to 18 carbon atoms, and with 1 to 5 glucoside units, sorbitan esters, such as polyethylene glycol sorbitan stearic, palmitic, myristic and lauric acid esters, fatty acid polyglycol esters or poly-condensates of ethyleneoxide and propyleneoxide, as they are on the market, for example, under the trade name "Pluronics®", as well as fatty alcohol ethoxylates, $C_{10}$-$C_{22}$-fatty alcohol ethoxylates, known by the generic terms "Laureth", "Myristeth", "Oleth", "Ceteth", "Deceth", "Steareth" and "Ceteareth" according to the CTFA nomenclature, including addition of the number of ethylene oxide molecules, e.g., "Laureth-16":

The average degree of ethoxylation thereby ranges between about 2.5 and about 100, preferably about 10 and about 30.

Suitable amphoteric surfactants are in particular the various known betaines such as alkyl betaines, fatty acid amidoalkyl betaines and sulfobetaines, for example, lauryl hydroxysulfobetaine; long-chain alkyl amino acids, such as cocoaminoacetate, cocoaminopropionate and sodium cocoamphopropionate and -acetate have also been proven suitable.

Suitable cationic surfactants are according to the general structure

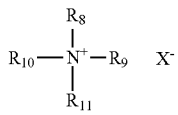

wherein $R_8$ is a saturated or unsaturated, branched or linear alkyl chain with 8-22 C atoms or $R_{12}$ CO NH $(CH_2)_n$ where $R_{12}$ is saturated or unsaturated, branched or linear alkyl chain with 7-21 C atoms and n has typical value of 1-4 or $R_{13}$ COO $(CH_2)_n$ where $R_{13}$ is saturated or unsaturated, branched or linear alkyl chain with 7-21 C atoms and n has typical value of 1-4, and $R_9$ is H or unsaturated or saturated, branched or linear alkyl chain with 1-22 C atoms or $R_{12}$ CO NH $(CH_2)_n$ or $R_{13}$ CO O $(CH_2)_n$ where $R_{12}$, $R_{13}$ and n are same as above.

$R_{10}$ and $R_{11}$ are H or lower alkyl chain with 1 to 4 Carbon atoms, and X is typically chloride, bromide, methosulfate.

Typical examples of those ingredients are cetyl trimethyl ammonium chloride, stearyl trimonium chloride, dipalmitoyl dimonium chloride, distearyl dimethyl ammonium chloride, stearamidopropyl trimonuim chloride, dioleoylethyl dimethyl ammonium methosulfate, dioleoylethyl hydroxyethylmonium methosulfate.

The total concentration of one or more surfactants is in the range of 0.1 to 5%, preferably 0.2 to 4% and most preferably 0.2-2.5% by weight, calculated to the total composition.

The composition may comprise one or more ceramide compound, such as the one according to general formula

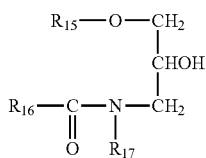

where $R_{15}$ and $R_{16}$ are independent from each other alkyl- or. alkenyl group with 10 to 22 carbon atoms, $R_{17}$ is alkyl or hydroxyl alkyl with 1 to 4 carbon atoms group and n is a number between 1 to 6, preferably 2 or 3. Preferred compound according to the above chemical structure is cetyl-PG-hydroxyethylpalmitamide. Concentration of ceramide type of compounds ranges from 0.01 to 2%, preferably 0.01 to 1% by weight calculated to total composition.

The composition may comprise ubiquinone of the formula:

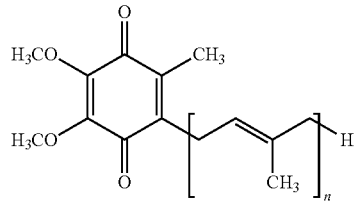

wherein n is a number from 1 to 10. Concentration of ubiquinone can vary between 0.001% and 10% by weight, calculated to the total of each composition.

The second object of the present invention is a method for coloring keratin fibers, preferably human keratin fibers, more preferably human hair, comprising the steps of:
a) mixing the composition of the present invention into an aqueous composition comprising one or more conditioning ingredients immediately prior to application onto hair,
b) applying thus obtained composition onto hair and leaving it on the hair for a period from 1 to 45 min, and
c) rinsing-off the composition from hair,
d) optionally shampooing the hair,
e) optionally drying the hair.

The composition of the present invention is mixed into an aqueous composition. The aqueous composition may be a conventional hair conditioning and or a cleansing composition. The hair conditioning compositions are known in general and widely being used. They are generally being a fatty alcohol and cationic surfactant based emulsion compositions which may comprise further known hair conditioners.

On the other hand, cleansing compositions are based on foaming cleansing surfactants such as anionic, non-ionic and amphoteric surfactants comprised generally at a concentration of approximately 20% by weight. Such compositions comprise furthermore hair conditioning compounds such as cationic polymers especially known with the CTFA adopted name as Polyquaternium.

Another possibility of colouring hair with the composition of the present invention is that the composition is mixed into an aqueous composition comprising one or more alkalizing agent. The suitable alkalizing agents are alkyl or alkanol amines as disclosed above and aqueous ammonia.

Further possibility of colouring hair with the composition of the present invention is the composition is mixed into an aqueous composition comprising one or more oxidative dye precursors and/or one or more oxidizing agent.

Suitable oxidative dye precursors classes are p-phenylendiamines, p-aminophenols, and heterocyclic compounds such as diaminopyrazols and substituted pyrimidines, and suitable coupling substances are resorcinols, m-aminophenols, m-phenylendiamines, pyridines and substituted derivatives, and naphthols.

Non-limiting examples of the oxidative dye precursor compounds are p-phenylenediamine, p-aminophenol, 2,5-diamino-toluene, 2-n-propyl or 2-ethyl-p-phenylenediamine, 2,6-di-methyl-p-phenylene-diamine, 2-(2,5-diaminophenyl) ethanol, 1-amino-4-bis-(2'-hydroxy-ethyl)aminobenzene, 2-(2-hydroxyethyl amino)-5-aminotoluene, 4,4'-diaminodiphenylamine, 4-aminodiphenylamine, 2-amino-5-N,N-diethyl aminotoluene, 4-amino-N-ethyl-N-isopropyl aniline, 2-chloro-p-phenylendiamine, 1-β-hydroxyethyl-2, 5-diamino-4-chlorobenzene, 1-β-hydroxyethyl-2,5-di-amino-4-methyl benzene, 2-methoxy-p-phenylenediamine, N,N-diethyl-p-phenylenediamine, 1-amino-4-β-methoxyethyl aminobenzene, 1-dimethyl-amino-4-aminobenzene, 1-hydroxy-2,5-diamino-4-methyl benzene, 1-hydroxymethyl-2,5-diaminobenzene, 1,3-dimethyl-2,5-diaminobenzene, 1,4-diamino isopropyl benzene and/or 1-amino-4-β-hydroxypropyl aminobenzene, 1-hydroxyethyl-4,5-diaminopyrazole, 3,4-diamino-5-hydroxypyrazole, 3,5-diaminopyrazole, 3,5-diamino pyrazol-1-carboxamide, 3-amino-5-hydroxypyrazole, 1-phenyl-2-methylpyrazole, 1-phenyl-3-methylpyrazole-5-one, 3,5-dimethylpyrazole, 3,5-dimethylpyrazole-1-methanol, 3,5-diamino-1,2,4-triazole, 4-aminophenol and the derivatives thereof such as 4-amino-3-methylphenol, 2-chloro-4-aminophenol, 2,6-dichloro-4-aminophenol, 2,4-diamino-phenol, 2,6-dibromo-4-aminophenol, tetraamino pyrimidines, triaminohydroxy pyrimidines, diaminomono- and -dihydroxy pyrimidines, aminotriazines, 5-amino salicylic acid and/or 1,2,4-triamino benzene, 2,5-diaminopyridine, 2,3-diaminopyridine, 2,6-diaminopyridine, 3-amino-2-methyl amino-6-methoxypyridine, 2-dimethyl-5-aminopyridine, 2-dimethyl aminoethyl-3-hydroxypyridine, 2-amino-4,6-dimethyl pyridine, 2-amino-3-hydroxypyridine, 3-amino-2(β-hydroxyethyl amino)-6-methoxy pyridine, 2,6-dimethyl amino-5-aminopyridine, 2-di(hydroxyethyl) amino-5-aminopyridine, 2-hydroxyethyl amino-5-aminopyridine, 4-hydroxy-2,5,6-triaminopyrimidine and/or the water-soluble salts thereof, and mixture thereof.

The total concentration of the dye precursors (developing substances) customarily ranges between 0.001 to 5%, preferably 0.01 to 4% and more preferably 0.05 to 3%, and most preferably 0.1 to 2% by weight, calculated to the total composition.

The aqueous composition comprising the oxidative dye precursor may further comprise coupling substances. The suitable non-limiting examples of the coupling substance if present in the composition A are 5-amino-2-methylphenol, 2-methyl-5-hydroxyethylaminophenol, 2,4,-diaminophenoxyethanol, 2-amino-4-hydroxyethylaminoanisol, 2-methyl-5-amino-6-chlorphenol, 1,3-bis(2,4-diaminophenoxy)propane, 2-bis(2-hydroxyethyl)aminotoluene, 2-amino-5-methylphenol, resorcinol, 2-methyl-resorcinol, 4-chlororesorcinol, 2-amino-4-chlorophenol, 5-amino-4-methoxy-2-methylphenol, 2-aminophenol, 3-amino-phenol, 1-methyl-2-hydroxy-4-aminobenzene, 3-N,N-dimethyl aminophenol, 2,6-dihydroxy-3,5-dimethoxypyridine, 5-amino-3-methylphenol, 6-amino-3-methylphenol, 1,3-diamino-benzene, 1-amino-3-(2'-hydroxyethylamino)benzene, 1-amino-3-[bis(2'-hydroxy-ethyl) amino]benzene, α-naphthol, 4,6-dichlororesorcinol, 1,3-diamino-toluene, 4-hydroxy-1,2-methylenedioxy benzene, 1,5-dihydroxy naphthalene, 1,6-dihydroxy naphthalene, 1,7-dihydroxy naphthalene, 2,7-dihydroxy naphthalene, 1-hydroxy-2-methyl naphthalene, 4-hydroxy-1,2-methyldioxy benzene, 2,4-diamino-3-chlorophenol, 5-amino-2-methoxyphenol and/or 1-methoxy-2-amino-4-(2'-hydroxyethyl amino)benzene or the water-soluble salts thereof and mixture thereof.

The coupling substance are present in approximately the same molecular proportions as the developing substances, i.e. at a total concentration in the range of 0.001 to 5%, preferably 0.01 to 4% and more preferably 0.05 to 3%, and most preferably 0.1 to 2% by weight, calculated to the total composition.

The composition of the present invention is mixed into an aqueous composition comprising one or more oxidizing agents. The oxidizing agents suitable are hydrogen peroxide, urea peroxide, melamin peroxide or perborate salts. The most preferred is hydrogen peroxide. The aqueous composition comprises one or more oxidizing agents at a total concentration of 1 to 20% by weight, preferably 2 to 15%, more preferably 2 to 12% and most preferably 3 to 12% by weight, calculated to total of the aqueous composition. The aqueous composition may be in the form of a solution, thickened gel or an emulsion. Emulsion form is particularly preferred. The aqueous composition comprising one or more oxidizing agents has a pH in the range of 2 to 5.

The third object of the present invention is a method for bleaching and colouring keratin fibers, preferably human keratin fibers, more preferably human hair comprising the steps of a—mixing the composition of the present invention with two other compositions wherein one of the compositions is an anhydrous powder composition comprising one or more persalts and the other composition is an aqueous composition comprising one or more oxidizing agent, b—applying thus obtained composition onto hair and leaving it on the hair for a period from 1 to 45 min, and c—rinsing-off the composition from hair, d—optionally shampooing the hair, e—optionally drying the hair.

The anhydrous powder composition comprises one or more persalts. Useful are sodium persulfate and potassium persulfate and ammonium persulfate, earth alkali peroxides such as magnesium peroxide, melamine peroxide or urea peroxide or phtholimidoperoxy hexanoic acid. The preferred persalts are sodium persulfate and potassium persulfate. The persalt is comprised in the anhydrous composition at a total concentration in the range of 10 to 80%, preferably 15 to 70%, more preferably 20 to 60% and most preferably 25 to 60% by weight, calculated to total of composition A.

The composition is furthermore mixed with an aqueous composition comprising one or more oxidizing agent as described above.

The fourth objective of the present invention is a kit comprising an individually packed composition of the present invention, and one or more of the following individually packed compositions a—an aqueous composition comprising one or more conditioning ingredients b—an aqueous composition comprising one or more alkalizing agents c—an aqueous composition comprising one or more oxidative dye precursors, d—an aqueous composition comprising one or more oxidizing agents, and e—an anhydrous powder composition comprising one or more persalts.

The aqueous composition comprising one or more conditioning compounds is a cleansing or a conditioning composition used after hair cleansing. Both compositions are briefly defined above.

The compositions referred under b, c, d and e are also defined above.

The following examples are to illustrate the invention but not to limit.

EXAMPLE 1

| Ingredient | % by weight |
|---|---|
| Aminomethyl propanol | 5.0 |
| HC Red 18 | 2.0 |
| HC Yellow 16 | 0.5 |

-continued

| Ingredient | % by weight |
| --- | --- |
| Fragrance | q.s. |
| 1,2-propylene glycol | to 100 |

The above composition was prepared by dissolving all the ingredients in 1,2-propylene glycol. The pH measured as 10% by weight solution in demineralized water was 10.2. The above composition comprises less than 1% by weight water.

Stability tests of the above composition at 5° C., 20° C., 40° C. and 50° C. did not show any instability during the test period of 6 months. Microscopic evaluation showed no crystallization of the dyestuffs.

The above composition was mixed with the following cleansing composition at a weight ratio of the Example 1 to cleansing composition 2:10.

| Ingredient | % by weight |
| --- | --- |
| Sodium Laureth Sulphate | 12.0 |
| Sodium lauroyl sarcosinate | 3.0 |
| Lauryl hydroxyl sultaine | 1.5 |
| Ethyl hexyl glycerine | 0.9 |
| Amodimethicone | 0.3 |
| Lactic acid | q.s. to pH 5.5 |
| Water | to 100 |

The bleached human hair streak was washed with the obtained composition. The hair streak was colored red.

In the same way, the Example 1 was mixed into a hair conditioning composition having the following composition at a weight ratio of the Example 1 to conditioning composition 2:10.

| Ingredient | % by weight |
| --- | --- |
| Cetearyl alcohol | 10 |
| Cetrimonium chloride | 1 |
| Ceteareth-20 | 2 |
| Amodimethicone | 0.3 |
| Lactic acid | q.s. to pH 4.0 |
| Water | to 100 |

The bleached human hair streak was washed with the obtained composition. The hair streak was colored red.

EXAMPLE 2

| Ingredient | % by weight |
| --- | --- |
| Aminomethyl propanol | 7.5 |
| HC Red 18 | 2.0 |
| HC Yellow 16 | 0.5 |
| HC Blue 18 | 0.3 |
| Fragrance | q.s. |
| 1,2-propylene glycol | to 100 |

The above composition was prepared by dissolving all the ingredients in 1,2-propylene glycol. The pH measured as 10% solution in demineralized water was 10.9. The above composition comprises less than 1% by weight water.

The above composition was mixed with the following oxidizing composition at a weight ratio of Example 2 to oxidizing composition 1 to 1.

| Ingredient | % by weight |
| --- | --- |
| Cetearyl Alcohol | 1.7 |
| Mineral Oil | 2 |
| Glycerin | 0.5 |
| Etidronic Acid | 0.2 |
| Salicylic Acid | 0.02 |
| Phosphoric acid | 0.3 |
| Sodium Lauryl Sulfate | 0.2 |
| Hydrogen Peroxide | 6.0 |
| Water | Ad 100 |

The above composition has a pH 3.2.
The resulting composition had a pH 9.5.
The human hair streak having a natural colour at level 6 was colored with the composition thus obtained with a processing time of 30 min. The hair was colored red-brown.

Additionally the Example 2 was mixed with the above oxidizing composition and the following oxidative dyeing composition at a weight ratio of 1:3:2 (Example 2:Oxidizing composition: oxidative dyeing composition).

| Ingredient | % by weight |
| --- | --- |
| Cetearyl alcohol | 12 |
| Sodium Cetearyl Sulfate | 1.5 |
| Cocamide MEA | 5 |
| Propylene Glycol Stearate SE | 0.6 |
| Oleth-5 | 5.0 |
| Oleic Acid | 2.5 |
| Propylene Glycol | 1.0 |
| Tetrasodium EDTA | 0.2 |
| Ammonium Chloride | 0.5 |
| Sodium Sulfite | 0.8 |
| Ammonium Hydroxide | 5.0 |
| Toluene-2,5-Diamine sulfate | 0.74 |
| Resorcinol | 0.1 |
| 4-Chlororesorcinol | 0.24 |
| m-Aminophenol | 0.0 |
| 4-Amino-2-Hydroxytoluene | 0.02 |
| Perfume | q.s. |
| Water | Ad 100 |

The resulting composition had a pH 9.9.
The human hair streak having a natural colour at level 6 was colored with the composition thus obtained with a processing time of 30 min. The hair was colored red-brown.

Furthermore, the Example 2 was mixed with the above oxidizing composition and the following oxidative dyeing composition at a weight ratio of 1:3:2 (Example 2: Oxidizing composition: oxidative dyeing composition).

| Ingredient | Active matter % |
| --- | --- |
| Cetearyl Alcohol | 9.0 |
| Oleyl Alcohol | 4.0 |
| Octyldodecanol | 2.0 |
| Ceteareth-20 | 4.0 |
| Argania Spinosa Kernel Oil | 0.1 |
| Tetrasodium Glutamate Diaceate | 0.1 |
| Ethanolamine | 5.0 |
| Ascorbic Acid | 1.0 |
| Disodium Phosphate | 0.5 |
| Allantoin | 0.5 |
| Toluene-2,5-Diamine Sulfate | 1.0 |
| Resorcinol | 0.4 |
| m-Aminophenol | 0.08 |
| 2-Amino-3-Hydroxypyridine | 0.02 |
| Perfume | q.s. |
| Water | Ad 100 |

The resulting composition had a pH 9.5.

The human hair streak having a natural colour at level 6 was colored with the composition thus obtained with a processing time of 30 min. The hair was colored red-brown.

In a further test, the Example 2 was mixed with the above oxidizing composition and the following oxidative dyeing composition at a weight ratio of 1:3:2 (Example 2: Oxidizing composition: oxidative dyeing composition).

| Ingredient | % by weight |
| --- | --- |
| Cetearyl alcohol | 9.0 |
| Sodium Cetearyl Sulfate | 1.5 |
| Cocamide MEA | 3.0 |
| Oleic Acid | 1.00 |
| Tetrasodium EDTA | 0.2 |
| Sodium Sulfite | 0.5 |
| Potassium Iodide | 5.0 |
| Toluene-2,5-Diamine Sulfate | 1.0 |
| Resorcinol | 0.3 |
| m-Aminophenol | 0.1 |
| 4-Amino-m-cresol | 0.1 |
| 2-Amino-4-Hydroxyethylaminoanisole Sulfate | 0.1 |
| 2-Amino-3-Hydoxypyridine | 0.1 |
| HC Yellow 2 | 0.1 |
| Perfume | q.s. |
| Water | Ad 100 |

The resulting composition had a pH 7.5.

The human hair streak having a natural colour at level 6 was colored with the composition thus obtained with a processing time of 30 min. The hair was colored red-brown.

EXAMPLE 3

| Ingredient | % by weight |
| --- | --- |
| Aminomethyl propanol | 5.0 |
| HC Red 18 | 0.4 |
| HC Yellow 16 | 0.1 |
| HC Blue 18 | 1.0 |
| Fragrance | q.s. |
| 1,2-propylene glycol | to 100 |

The above composition was prepared by dissolving all the ingredients in 1,2-propylene glycol. The pH measured as 10% solution in demineralized water was 10.5. The above composition comprises less than 1% by weight water.

Stability tests of the above composition at 5° C., 20° C., 40° C. and 50° C. did not show any instability during the test period of 6 months. Microscopic evaluation showed no crystallization of the dyestuffs.

EXAMPLE 4

The Example 3 of above was mixed with an anhydrous bleaching composition of the following composition and the above presented oxidizing composition at a weight ratio of 1:2:3.

| Ingredient | % by weight |
| --- | --- |
| Ammonium persulfate | 21.00 |
| Potassium persulfate | 36.00 |
| Sodium metasilicate | 11.00 |
| Diatomaceous Earth | 21.00 |

-continued

| Ingredient | % by weight |
| --- | --- |
| Aerosil 380 | 1.00 |
| Liquid paraffin | 10.00 |

The resulting composition had a pH of 9.8.

Hair was bleached and coloured brownish.

The following examples are within the scope of the present invention. All compositions comprise less than 1% by weight water.

EXAMPLE 5

| Ingredient | % by weight |
| --- | --- |
| Aminomethyl propanol | 5.0 |
| HC Red 18 | 1.0 |
| HC Red 3 | 0.1 |
| Basic yellow 87 | 0.2 |
| Polysilicone-9 | 0.1 |
| Fragrance | q.s. |
| 1,2-propylene glycol | to 100 |

EXAMPLE 6

| Ingredient | % by weight |
| --- | --- |
| Monoethanolamine | 5.0 |
| HC Red 18 | 1.0 |
| HC Yellow 16 | 0.1 |
| HC Blue 18 | 1.0 |
| Amodimethicone | 0.1 |
| Fragrance | q.s. |
| 1,2-propylene glycol | to 100 |

EXAMPLE 7

| Ingredient | % by weight |
| --- | --- |
| Monoethanolamine | 5.0 |
| HC Blue 18 | 1.0 |
| Acid red 52 | 0.1 |
| 4-amino-3-nitrophenol | 0.2 |
| Sodium lauryl sulphate | 0.2 |
| Amodimethicone | 0.1 |
| Fragrance | q.s. |
| 1,2-propylene glycol | to 100 |

EXAMPLE 8

| Ingredient | % by weight |
| --- | --- |
| Monoethanolamine | 5.0 |
| HC Red 18 | 1.0 |
| Basic Blue 124 | 0.2 |
| HC Blue 17 | 0.8 |
| Sodium coco amphoacetate | 0.2 |
| 1,2-propylene glycol | to 100 |

EXAMPLE 9

| Ingredient | % by weight |
| --- | --- |
| Monoethanolamine | 5.0 |
| HC Yellow 16 | 1.0 |
| Acid red 52 | 0.1 |
| HC Yellow 2 | 0.5 |
| PEG-40 Hydrogenated castor oil | 0.2 |
| Polysilicone-9 | 0.1 |
| Fragrance | 0.5 |
| 1,2-propylene glycol | to 100 |

EXAMPLE 10

| Ingredient | % by weight |
| --- | --- |
| Monoethanolamine | 6.0 |
| Basic Red 51 | 1.0 |
| Picramic acid | 0.2 |
| PEG-60 Hydrogenated castor oil | 0.2 |
| Fragrance | 0.5 |
| 1,2-propylene glycol | to 100 |

EXAMPLE 11

| Ingredient | % by weight |
| --- | --- |
| Monoethanolamine | 5.5 |
| HC Red 18 | 0.5 |
| DC Yellow 10 | 1.5 |
| HC Red BN | 0.4 |
| Behentrimonium chloride | 0.2 |
| Fragrance | 0.3 |
| 1,2-propylene glycol | to 100 |

EXAMPLE 12

| Ingredient | % by weight |
| --- | --- |
| Monoethanolamine | 5.0 |
| HC Red 18 | 2.0 |
| Basic Violet 14 | 0.4 |
| 4-amino-23-nitro phenol | 0.1 |
| PEG-60 | 0.2 |
| Fragrance | 0.3 |
| 1,2-propylene glycol | to 100 |

EXAMPLE 13

| Ingredient | % by weight |
| --- | --- |
| Aminomethyl propanol | 5.0 |
| HC Red 18 | 0.4 |
| HC Yellow 16 | 0.1 |
| HC Blue 18 | 1.0 |
| Fragrance | q.s. |
| 1,3-propylene glycol | to 100 |

EXAMPLE 14

| Ingredient | % by weight |
| --- | --- |
| Aminomethyl propanol | 5.0 |
| HC Red 18 | 0.4 |
| HC Yellow 16 | 0.1 |
| HC Blue 18 | 1.0 |
| Fragrance | q.s. |
| Butylene glycol | to 100 |

EXAMPLE 15

| Ingredient | % by weight |
| --- | --- |
| Aminomethyl propanol | 5.0 |
| HC Red 18 | 0.4 |
| HC Yellow 16 | 0.1 |
| HC Blue 18 | 1.0 |
| Fragrance | q.s. |
| Pentylene glycol | to 100 |

EXAMPLE 16

| Ingredient | % by weight |
| --- | --- |
| Aminomethyl propanol | 5.0 |
| HC Red 18 | 0.4 |
| HC Yellow 16 | 0.1 |
| HC Blue 18 | 1.0 |
| Fragrance | q.s. |
| Hexylene glycol | to 100 |

EXAMPLE 17

| Ingredient | % by weight |
| --- | --- |
| Aminomethyl propanol | 5.0 |
| HC Red 18 | 0.4 |
| HC Yellow 16 | 0.1 |
| HC Blue 18 | 1.0 |
| Fragrance | q.s. |
| 1,3-propylene glycol | 20.0 |
| 1,2-Propylene glycol | to 100 |

EXAMPLE 18

| Ingredient | % by weight |
| --- | --- |
| Aminomethyl propanol | 5.0 |
| HC Red 18 | 0.4 |
| HC Yellow 16 | 0.1 |
| HC Blue 18 | 1.0 |
| Fragrance | q.s. |
| Butylene glycol | 20.0 |
| 1,2-Propylene glycol | to 100 |

EXAMPLE 19

| Ingredient | % by weight |
|---|---|
| Monoethanolamine | 5.0 |
| Ammonia* | 0.5 |
| HC Red 18 | 1.0 |
| HC Yellow 16 | 0.1 |
| HC Blue 18 | 1.0 |
| Amodimethicone | 0.1 |
| Fragrance | q.s. |
| 1,2-propylene glycol | to 100 |

*added as a 50% by weight solution in water.

The invention claimed is:

1. A composition, adapted for coloring keratin fibers, the composition comprising:
   one or more hair direct dyes is selected from at least one cationic dye, at least one anionic dye, at least one non-ionic dye and at least one nitro dye and present at a total concentration in the range of 0.001 to 10% by weight;
   one or more diols that is liquid at 20° C. at a total concentration more than or equal to 50% by weight; and
   2% by weight or less water, wherein all concentrations are calculated to a total weight of the composition
   wherein, the composition is liquid at 20° C.

2. The composition according to claim 1, wherein the one or more hair direct dyes is present as dissolved or partially dissolved in the one or more diols.

3. The composition according to claim 1, wherein the one or more hair direct dyes is selected from HC Red 18, HC Blue 18, and HC Yellow 16.

4. The composition according to claim 1, wherein the one or more diols is selected from $C_2$-$C_6$ diols, and linear or branched polymerization products of ethylene oxide and/or propylene oxide with a terminal OH group at both ends, and mixtures thereof.

5. The composition according to claim 1, wherein the at least one diols is 1,2-propylene glycol.

6. The composition according to claim 1, further comprising:
   an alkalizing agent selected from alkanolamines according to the general structure $R_4$ $R_5$ $R_6$ N wherein $R_4$, $R_5$ and $R_6$ are same or different H, $C_1$ to $C_4$ alkyl, $C_3$ to $C_4$ unsaturated alkyl, $C_3$ to $C_4$ branched alkyl, $C_1$ to $C_4$ hydroxy alkyl, $C_3$ to $C_4$ unsaturated hydroxy alkyl, $C_3$ to $C_4$ branched hydroxy alkyl, with the condition that at least one of $R_4$, $R_5$ or $R_6$ is different from H, at a concentration in the range of 0.5 to 15% by weight, calculated to the total weight of the composition.

7. The composition according to claim 6 wherein the alkalizing agent is monoethanolamine and/or aminomethyl propanol.

8. The composition according to claim 1, further comprising:
   one or more aminosilicone, selected from the following compounds a. a compound according to the general structure

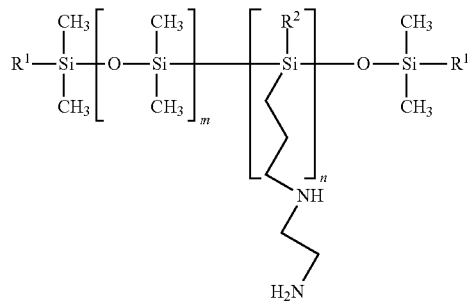

wherein $R^1$ is selected from OH, $OCH_3$, and/or O—Si—$(CH_3)_3$, $R^2$ is selected from $CH_3$, $OCH_3$, O—(Si—$(CH_3)_2$)x-R', and/or O—Si—$(CH_3)_3$, with the provision that if $R^1$ or $R^2$ are selected from O—Si—$(CH_3)_3$, then all other $R^1$ or $R^2$ are selected from O—Si—$(CH_3)_3$ and/or $OCH_3$;
   b. silicone graft copolymer comprising an organopolysiloxane segment as a main chain thereof and an unsaturated monomer-derived polymer segment as a side chain thereof, that is obtainable by firstly reacting an aminopropyl dimethicone with the thiolactone of acetyl homocysteine and then graft copolymerizing the thus obtained mercapto modified dimethicone with a mixture of N,N dimethylacrylamide and N-t-butylacrylamide; and
   c. an organopolysiloxane, wherein at least two silicon atoms in an organopolysiloxane segments constituting a main chain of the organopolysiloxane are bound to poly(N-acylalkyleneimine) segments consisting of repeating units represented by the following general formula via alkylene group containing hetero atom:

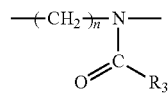

wherein $R_3$ is a hydrogen atom, an alkyl group having 1 to 22 carbon atoms, an aralkyl group, or an aryl group; and n is 2 or 3;
   wherein the number-average molecular weight of the poly-(N-acylalkyleneimine) segment is from 1,200 to 5,500,
   wherein the weight ratio of the organopolysiloxane segments (a) constituting the main chain to the poly-(N-acylalkyleneimine) segments (b) is from 35/65 to 60/40,
   wherein the weight-average molecular weight of the adjacent poly-(N-acylalkyleneimine) segments is from 1,300 to 5,500, and
   wherein the weight-average molecular weight of the organopolysiloxane segment constituting the main chain is from 7,000 to 100,000.

9. The composition according to claim 1, wherein the composition has a pH in the range of 9 to 11 measured as a 10% by weight solution in demineralised water at 20° C.

10. The composition according to claim 1, further comprising:
    one or more surfactants selected from at least one anionic surfactant, at least one non-ionic surfactant, at least one cationic surfactant and at least one amphoteric surfactant, wherein the one or more surfactants is present at a concentration in the range of 0.1 to 5% by weight, calculated to the total weight of the composition.

11. A method for coloring keratin fibers, the method comprising:
- a) mixing the composition of claim 1 into an aqueous composition comprising one or more conditioning ingredients immediately prior to application onto hair;
- b) applying thus mixed composition onto hair and leaving it on the hair for a period from 1 to 45 min; and
- c) rinsing-off the composition from the hair.

12. The method according to claim 11 wherein the aqueous composition comprises at least one selected from one or more oxidative dye precursors and one or more oxidizing agent.

13. A method for bleaching and colouring keratin fibers, the method comprising:
- a—mixing the composition of claim 1 with two other compositions wherein a first composition of the other compositions is an anhydrous powder composition comprising one or more persalts and a second composition of the other composition is an aqueous composition comprising one or more oxidizing agent;
- b—applying thus mixed composition onto hair and leaving it on the hair for a period from 1 to 45 min; and
- c—rinsing-off the composition from the hair.

14. A kit comprising:

the composition of claim 1, individually packaged; and one or more of the following individually packed compositions:
- a—an aqueous composition comprising one or more conditioning ingredients;
- b—an aqueous composition comprising one or more alkalizing agents;
- c—an aqueous composition comprising one or more oxidative dye precursors;
- d—an aqueous composition comprising one or more oxidizing agents; and
- e—an anhydrous powder composition comprising one or more persalts.

* * * * *